United States Patent [19]

Krahn

[11] 4,045,130
[45] Aug. 30, 1977

[54] APPARATUS FOR THE PERIMETRIC TESTING OF THE VISUAL FIELD OF THE HUMAN EYE

[75] Inventor: Wilhelm Krahn, Hamburg, Germany

[73] Assignee: Optische Werke G. Rodenstock, Germany

[21] Appl. No.: 584,860

[22] Filed: June 9, 1975

[30] Foreign Application Priority Data

June 12, 1974 Germany .............................. 2428441

[51] Int. Cl.² ............................................... A61B 3/02
[52] U.S. Cl. ....................................... 351/24; 351/36
[58] Field of Search ....................... 351/24, 39, 23, 30, 351/31, 36

[56] References Cited

U.S. PATENT DOCUMENTS

| | | | |
|---|---|---|---|
| 3,284,154 | 11/1966 | Friedmann | 351/31 X |
| 3,300,269 | 1/1967 | Schultz | 351/24 |
| 3,416,857 | 12/1968 | Lookabaugh | 351/31 |
| 3,421,498 | 1/1969 | Gans | 351/24 X |
| 3,664,732 | 5/1972 | Lynn | 351/24 X |

Primary Examiner—Paul A. Sacher
Attorney, Agent, or Firm—Craig & Antonelli

[57] ABSTRACT

A perimetric testing apparatus is described for use in testing the field of vision of human eyes. This apparatus includes an approximately hemispherical shell together with a device for projecting successive light pattern groups onto the inner surface of the shell. The device includes shadow masks, representative of different light pattern groups, which may be selectively inserted into the light path of a light source projector. The apparatus may be used in a dynamic perimeter.

20 Claims, 25 Drawing Figures

APPARATUS FOR THE PERIMETRIC TESTING OF THE VISUAL FIELD OF THE HUMAN EYE

This invention relates to an apparatus for perimetric testing of the field of vision of human eyes wherein the person to be tested, or test person, is subjected to varying groups of light signals in succession, appearing on the inner surface of an approximately hemispherical shell.

BACKGROUND OF THE INVENTION

It has been known from German Pat. No. 1,229,753 to expose a test person for a short period of time to individual light spots in succession, appearing on the inner surface of a hemispherical shell. For this purpose, it is possible to arrange a plurality of light sources in the surface of the half shell, wherein these light sources are illuminated individually with the aid of an electronic control device. Alternatively, the individual light spots are projected into the half shell with the aid of a pivotable projector. The provision of several light spots simultaneously has not been contemplated in this reference.

In German Pat. No. 1,184,114 an apparatus is described wherein certain groupings of light spots are made to appear for a short period on a planar area which is not shielded laterally with respect to the person to be tested. The variation of different light spot groupings is therein accomplished by the mutual rotation of superimposed gratings which are correspondingly perforated. The light source is a flashtube arranged in a box behind the gratings. Due to the mechanical structure, it is practically impossible to control the eye to be tested with respect to its direction of fixation.

An arrangement is shown in U.S. Pat. No. 3,025,755 wherein the test person is subjected to light spots appearing in groups on a planar observation surface, which is not screened off laterally. For this purpose, the observation area is subdivided on its backside into varying fields wherein there are disposed respectively one or several incandescent lamps. These incandescent lamps are switched on in varying combinations.

Further, in German Pat. No. 1,202,024 a perimeter is described wherein the eye to be examined is subjected to various combinations of light spots for a short period of time; these light spots appear on a surface having the shape of a spherical segment. The light spots are illuminated by a common light source by way of a condenser lens. A rotatable perforated (Nipkow) disk in the light flux serves for selecting the light spot combinations. A selection of light spots, which can be made to appear in groups by rotating the perforated disk, is lit up with the aid of light conducting rods.

SUMMARY OF THE INVENTION

It is an object of this invention to provide an apparatus for the static-perimetric testing of the visual field of the human eye with the aid of light spot groups made to appear for a short time within a concave projection area, wherein the light signals can be offered in a plurality of combinations with regard to position, brightness, size, and contrast with respect to the brightness of the inner surface of the concave shell. In this connection, control of the position of the eye to be tested is also to be possible during the appearance of the signal. Moreover, the combination of the apparatus of this invention with a dynamic perimeter is feasible.

This object is attained, in accordance with the invention, by providing a light signal projector which projects onto the inner surface of the shell. The image angle of this projector covers the region of the shell corresponding to the essential portion of the visual field of the eye to be tested. This projector further comprises in its object plane exchangeable shadow masks or the like associated with the individual groups of light signals.

The light source for the light signal projector can be an electronic flash arrangement; it is also possible to utilize a continuous light source in conjunction with a shutter adjustable to various opening times.

The light source can be fashioned to emit monochromatic light or constructed in connection with corresponding filters so that is emits monochromatic light.

A number of shadow masks, each of which is associated to a group of light signals, can be provided in a common shadow mask carrier which latter, in turn, is arranged to be displaceable within the projector and can be advanced mechanically from one shadow mask to the next. Such a shadow mask carrier can be constructed as a linearly movable slide or as a circular disk rotatable about its axis. The shadow mask carrier can be driven manually or mechanically, wherein the mechanical drive can be associated with a remote control device.

The projected light signals can be controllable in their brightness, just as the illumination of the inner surface of the shell. Furthermore, the time period for which the light signals are offered can be variable.

The apparatus of the present invention is especially suitable for an attachment to a perimeter construction having an approximately hemispherical projection screen.

BRIEF DESCRIPTION OF THE DRAWINGS

The drawings show various non-limitive embodiments of the invention, to wit.

DESCRIPTION OF THE PREFERRED EMBODIMENTS

Figure 1:
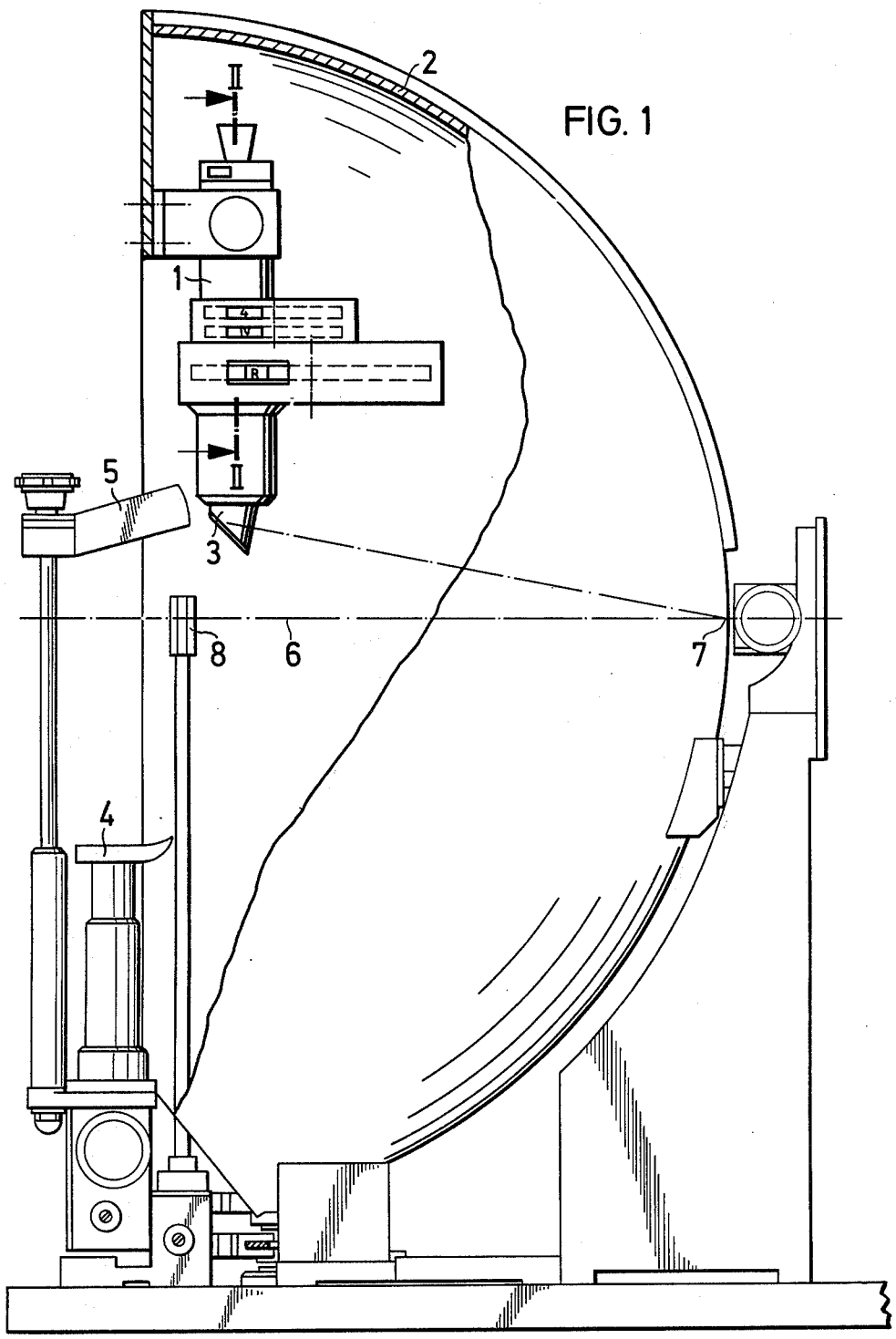
FIG. 1 shows a lateral view of the present invention with the hemispherical projection screen, partially broken away.

In detail, FIG. 1 illustrates the light signal projector 1 arranged in the upper zone of an approximately hemispherical shell 2 serving as the projection screen. The optical beam path extending in the interior of the light signal projector from the top toward the bottom is directed, in the lower zone thereof, onto the shell 2 by means of a deviating prism 3. The apparatus comprises in a conventional manner an adjustable chin rest 4, as well as a likewise adjustable head support 5. The eye to be examined is to be disposed in the line of symmetry 6 of the shell 2 and is to fix on the center 7. Corrective lenses can be inserted in a holder 8.

Figure 2:
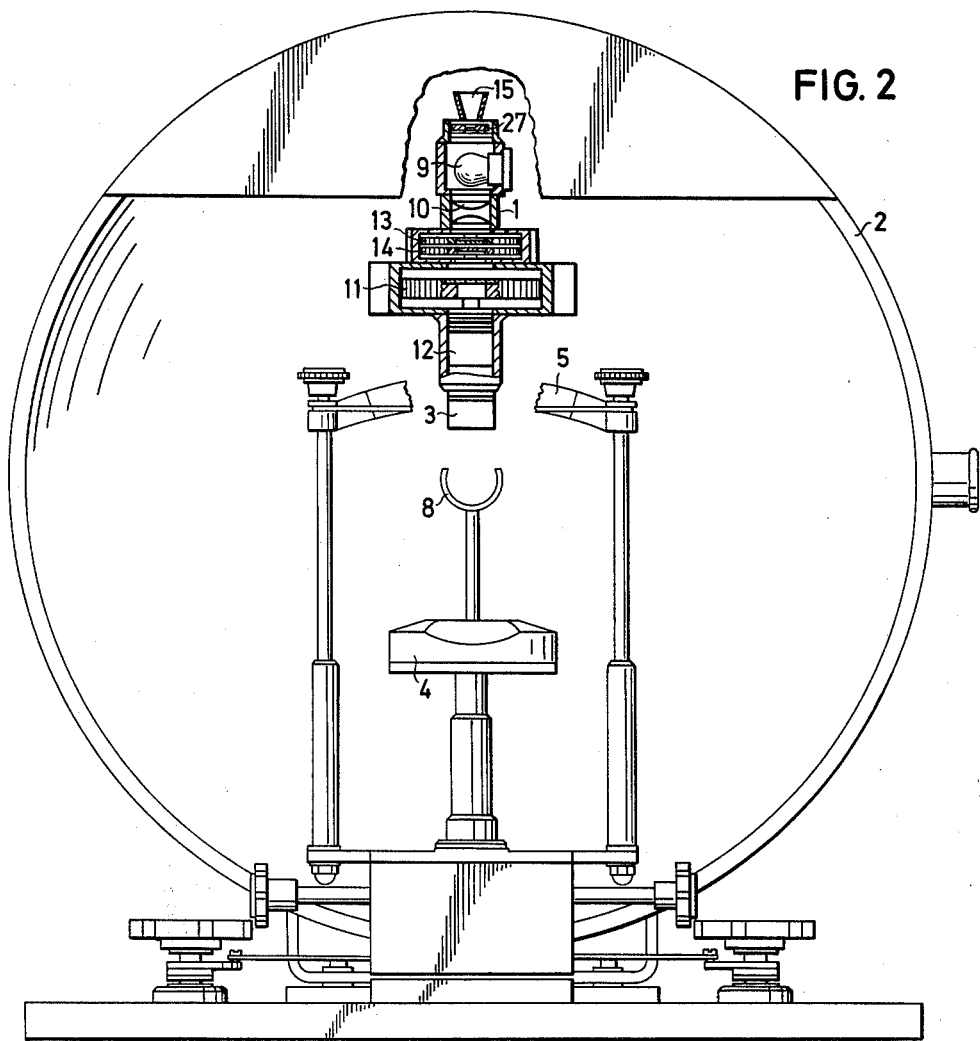
FIG. 2 shows a front view of the arrangement illustrated in FIG. 1 with a section through the projector along the plane II—II in FIG. 1.

In the front view of FIG. 1, shown in FIG. 2, the projector 1 is shown in a section along the plane II—II (FIG. 1). The light source 9, which may be an electronic flash arrangement or a continuous light source having a timed shutter arrangement, illuminates with the aid of a condenser arrangement 10 the shadow masks disposed in the shadow mask carrier 11, fashioned as a circular disk. The light is projected as images corresponding to different light signal groups onto the shell 2 with the aid of the objective 12 and the deviating prism 3. The shadow mask carrier 11 may be rotated to position selected shadow masks within the optical path, either manually or mechanically such as by means of a remote control device (not shown). In addition, the shadow mask carrier 11 may be constructed in a linear slide arrangement movable in the object plane of the projector 1. Brightness and color of the thus-projected light signals can be changed by rotatable filter disks 13 and 14, thereby varying the light intensity of the light signals, as well as enabling a changeable monochromatic light signal.

From the light source 9, light can also pass through a diaphragm arrangement 27, which may be adjustable, and a light exit tunnel 15 into the shell so that the latter can have an adjustable basic brightness of a predetermined intensity. Since the general illumination of the shell and the projection of the light signals emanate from a common light source 9, the contrast of the light signals with respect to the shell illumination is essentially maintained even in case of brightness fluctuations of the light source 9.

Figure 3:
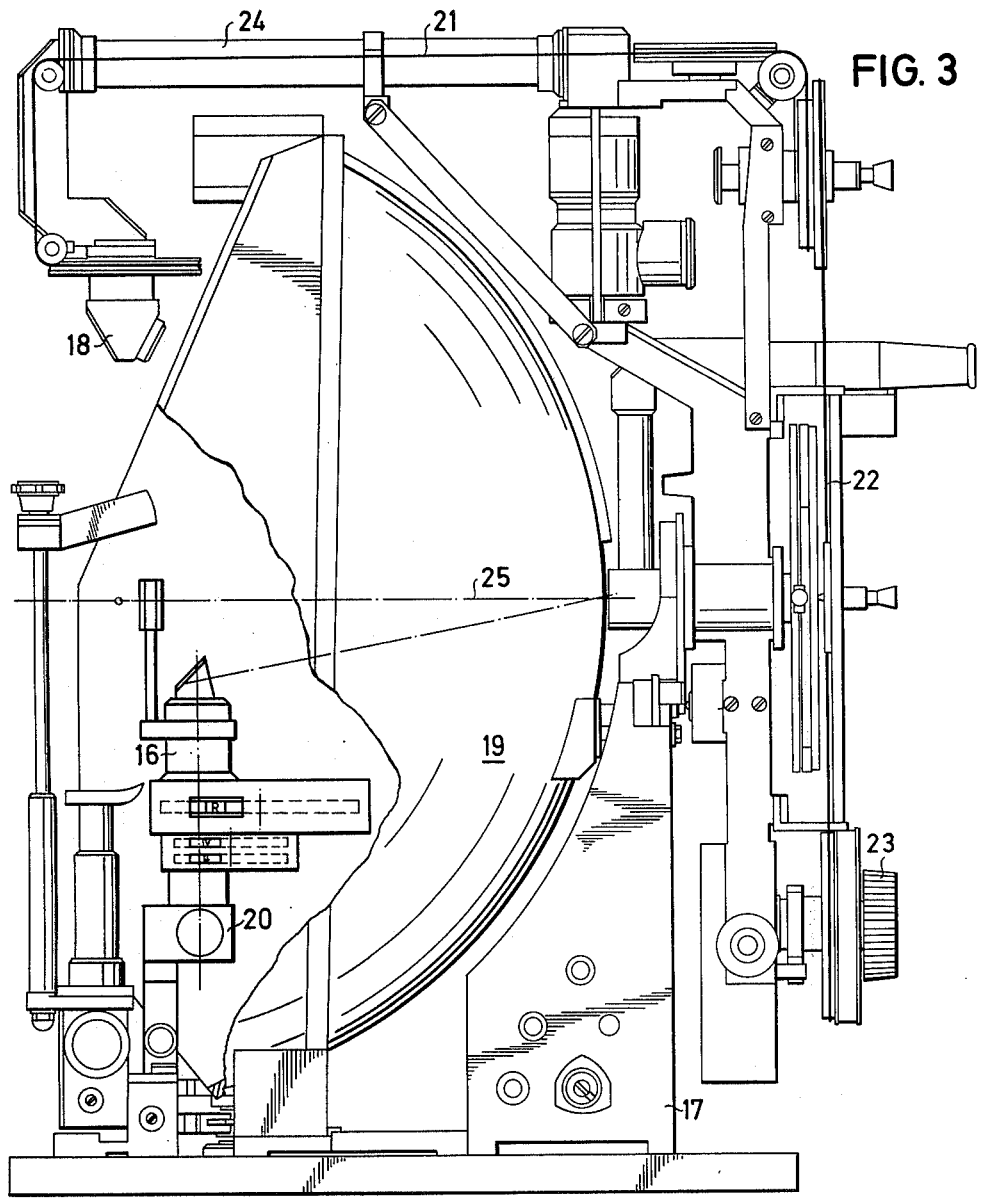
FIG. 3 shows another embodiment of the invention wherein the projector is arranged as an attachment in a customary dynamic perimeter.

FIG. 3 shows the arrangement of the light signal projector 16 in accordance with the invention as a supplemental attachment to a dynamic perimeter 17 which may be of a conventional type. The light signal projector 16 corresponds entirely to the previously described light signal projector 1 (FIGS. 1 and 2); however, for example, the diaphragm arrangement 27 and the light exit tunnel 15 are not included in this arrangement.

In order not to impair the function of the pivotable projector 18 of the dynamic perimeter 17, the light signal projector 16 is here located in the lower zone of the approximately hemispherical shell 19, illustrated as being broken away, and is mounted with the aid of an appliance or instrument holder 20. The pivotable projector 18 operates in the dynamic perimeter 17 for projecting a movable light signal within the shell 19. The projector 18 is driven by way of continuous rope-pulley devices 21 and 22, on the one hand, with the aid of the operating handle 23, and, on the other hand, by pivoting the entire projector support 24 about the axis 25.

Figure 4:
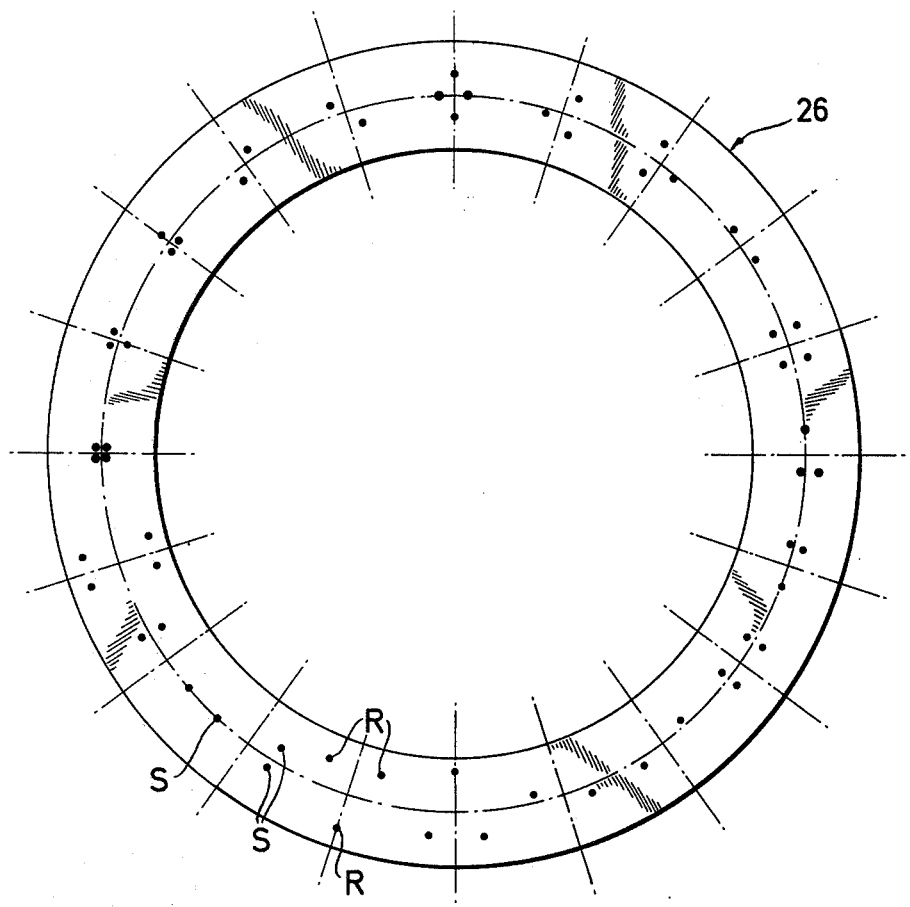
FIG. 4 shows a schematic representation of a shadow mask carrier fashioned as a circular disk.

FIG. 4 shows schematically a shadow mask carrier 26 of the type that may be utilized in this invention, having the shape of a circular disk wherein, for example, two perforated or light-permeable zones, associated respectively with one light signal group, are denoted by S and R.

Figure 5:
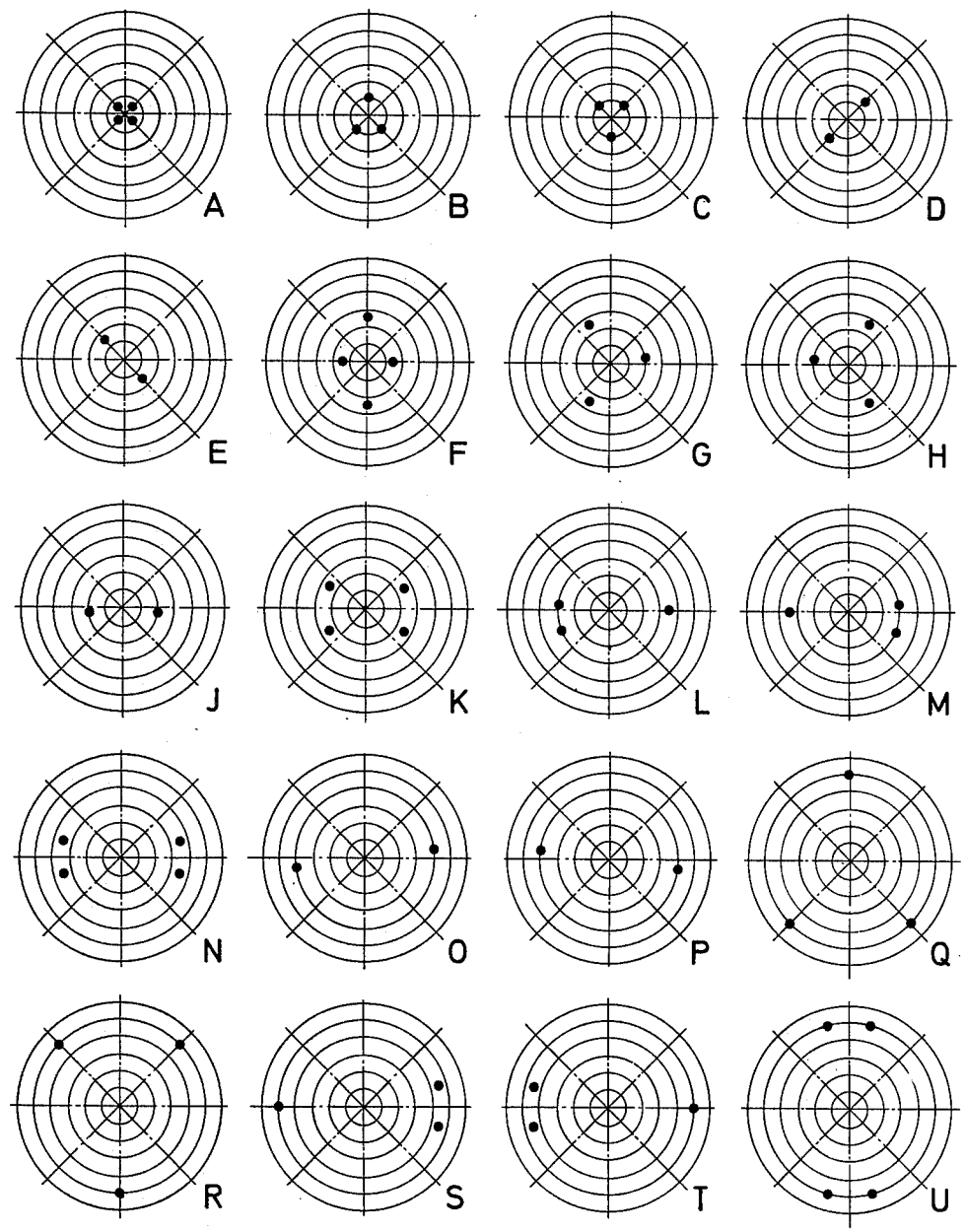
FIGS. 5A-5U show a number of various light signal groups.
Figure 6:
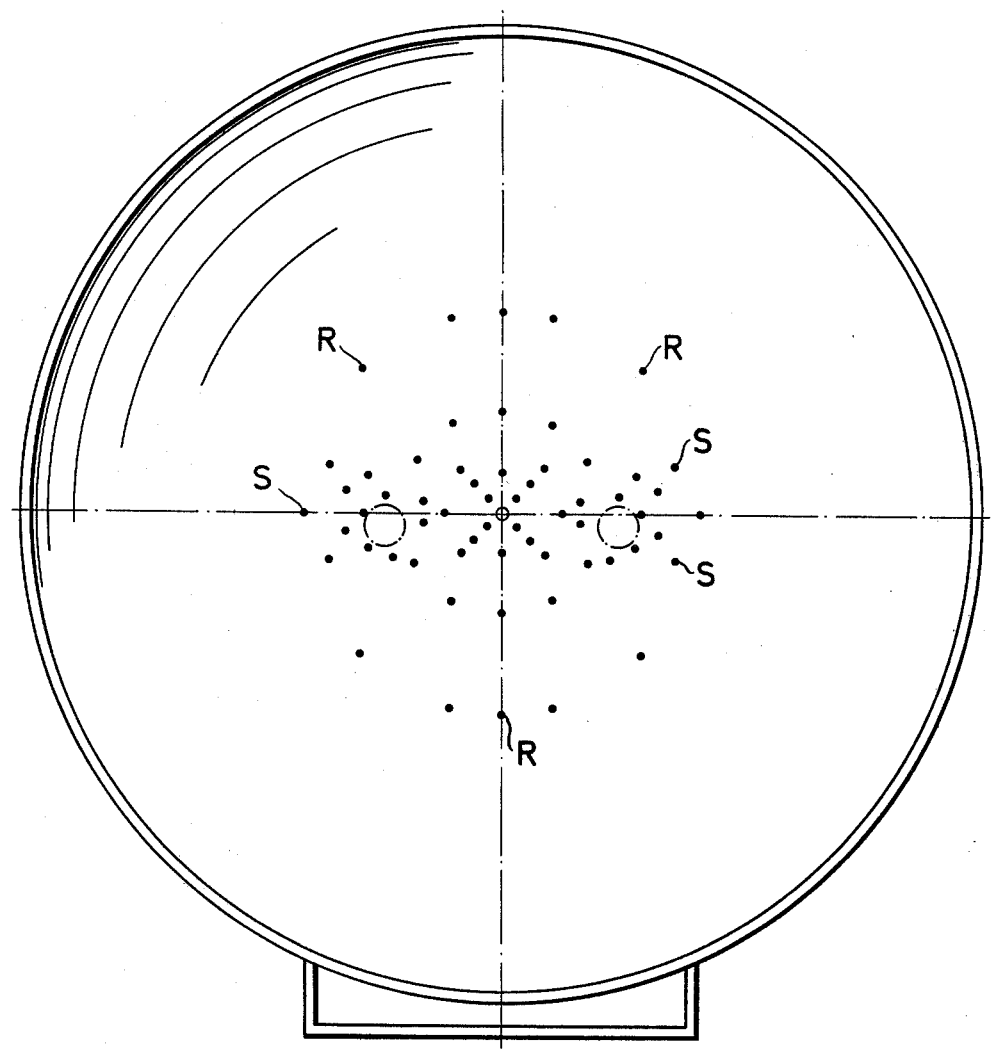
FIG. 6 shows a total distribution of all groups indicated in FIG. 5.

FIG. 5 shows schematically different light signal groups, each of which consists of two to four light signals which are in a specific arrangement or pattern with respect to one another. (Groups R and S, for example, see FIG. 4.) The individual light signal groups A-U, illustrated in FIG. 5, can be offered to the person to be tested in succession. In this case, the scanning of the essential portion of the visual field of the eye to be tested is obtained as illustrated in FIG. 6. The distribution of the light signals is such that the scanning operation is denser or more concentrated in the physiologically important zone of the visual field than in the marginal zones.

When using the arrangement of the light signal projector of this invention, as shown in FIG. 3, for an attachment to a dynamic perimeter, a visual field deficiency (scotoma), determined by the rapidly conducted static perimetry, can be accurately diagnosed with the aid of subsequent dynamic perimetry, without requiring the test person to be examined sequentially with separate instruments.

While I have shown and described several embodiments in accordance with the present invention, it is understood that the same is not limited thereto but is susceptible of numerous changes and modifications as known to a person skilled in the art, and I therefore do not wish to be limited to the details shown and described herein but intend to cover all such changes and modifications as are obvious to one of ordinary skill in the art.

I claim:

1. An apparatus for perimetric testing of the field of vision of eyes comprising:
an approximately hemipherical shell; and
means for successively projecting selected individual ones of a plurality of patterns of light spots wherein each of said patterns comprise a plurality of light spots on the inner surface of said hemispherical shell at an angle corresponding to the visual field of the eye to be tested, said projecting means including means for controlling the light spots of each pattern as to brightness of position, size, and contrast with respect to the brightness of the inner surface of said hemispherical shell.

2. An apparatus according to claim 1, wherein said successively projecting means includes
light source means for selectively providing a light signal, and
shadow mask means, disposed at the object plane of said projecting means, for successively positioning a respective one of a plurality of shadow masks in the light path of said light source means, each respective shadow mask corresponding to one of said patterns of light spots.

3. An apparatus according to claim 2, wherein said light source means includes an electronic flash means for providing said light signal in selectively timed sequence.

4. An apparatus according to claim 2, wherein said light source means includes a continuous light source and shutter means for providing siad light signal from said continuous light source at selectively variable opening times.

5. An apparatus according to claim 2, wherein said projecting means includes means for providing said light signal as a selectively variable monochromatic light signal.

6. An apparatus according to claim 5, wherein said means for providing said monochromatic light signal is a monochromatic light source.

7. An apparatus according to claim 5, wherein said means for providing said monochromatic light signal includes exchangeable filter means disposed in said light path of said light signal for varying the monochromatic characteristic of said light signal.

8. An apparatus according to claim 2, wherein said shadow mask means includes carrier means for holding said plurality of shadow masks, each of said plurality of shadow masks corresponding to different respective ones of said patterns of light spots.

9. An apparatus according to claim 8, wherein said carrier means is movably arranged in said projecting means, each of said plurality of shadow masks being selectively switched between adjacent ones of said shadow masks.

10. An apparatus according to claim 9, wherein mechanical drive means are provided for selectively switching said shadow masks.

11. An apparatus according to claim 10, wherein said mechanical drive means comprises a remote control device.

12. An apparatus according to claim 8, wherein said carrier means includes a circular disk structure rotatable in said object plane of said projecting means.

13. An apparatus according to claim 8, wherein said carrier means includes a linear slide structure linearly movable in said object plane of said projecting means.

14. An apparatus according to claim 2, wherein said projecting means includes means for providing said light signal as a selectively variable monochromatic light signal.

15. An apparatus according to claim 14, wherein said means for providing said monochromatic light signal is a monochromatic light source.

16. An apparatus according to claim 15, wherein said means for providing said monochromatic light signal includes exchangeable filter means disposed in said light path of said light signal for varying the monochromatic characteristic of said light signal.

17. An apparatus according to claim 2, wherein said projecting means includes filter means disposed in said light path of said light signal for selectively controlling the brightness of said light signal.

18. An apparatus according to claim 2, wherein means are provided for controlling the illumination of said inner surface of said hemispherical shell, such that contrast between the illuminated inner surface and said patterns of light spots can be regulated.

19. An apparatus according to claim 18, wherein said means for controlling the inner surface illumination of said hemispherical shell include means for providing a portion of said light signal on said inner surface separate from said shadow mask means.

20. An apparatus according to claim 1, further comprising a dynamic perimeter including second movable projecting means associated with said hemispherical shell, wherein said means for successively providing said patterns of light spots is arranged in cooperation with said second movable projecting means.

* * * * *